United States Patent [19]
Cromer et al.

[11] Patent Number: 5,972,630
[45] Date of Patent: Oct. 26, 1999

[54] HOMOGENEOUS IMMUNOASSAYS USING ENZYME INHIBITORS

[75] Inventors: Remy Cromer, San Jose; Rohan Peries, Mountain View; Dariush Davalian, San Jose; Carl N. Skold, Mountain View; Edwin F. Ullman, Atherton; Kesavan Radika, Mountain View, all of Calif.

[73] Assignee: Dade Behring Marburg GmbH, Marburg, Germany

[21] Appl. No.: 07/747,082

[22] Filed: Aug. 19, 1991

[51] Int. Cl.$^6$ .............. C07K 16/00; C12Q 1/00; C12Q 1/54
[52] U.S. Cl. .......... 435/7.71; 435/7.1; 436/503; 436/536; 530/387.1
[58] Field of Search .............. 435/7.1, 7.4, 7.71, 435/7.72, 7.9, 207; 530/387, 402, 391.3, 391.7, 387.1; 436/503, 536

[56] References Cited

U.S. PATENT DOCUMENTS

| | | | |
|---|---|---|---|
| 4,203,802 | 5/1980 | Rubenstein | 435/188 |
| 4,376,165 | 3/1983 | Hornby | 435/188 |
| 4,430,263 | 2/1984 | March et al. | 530/300 |
| 4,686,181 | 8/1987 | Doná | 435/7.71 |
| 4,785,080 | 11/1988 | Farina | 530/402 |
| 5,098,828 | 3/1992 | Geiger | 435/7.72 |

FOREIGN PATENT DOCUMENTS

| | | |
|---|---|---|
| 0 154 276 A3 | 9/1985 | European Pat. Off. . |
| 0 245 981 A3 | 11/1987 | European Pat. Off. . |
| 0 271 731 A3 | 6/1988 | European Pat. Off. . |
| 0 272 691 A2 | 6/1988 | European Pat. Off. . |
| 1 595 101 | 8/1981 | United Kingdom . |

OTHER PUBLICATIONS

Ngo, et al., *FEBS Letters* Jul. 1980, vol. 116(2), 285–288.

Skold, et al., *Journal of Immunology* May 1987, vol. 138, 3408–3414.

Wei, et al., *Clincial Chemistry* 1977, vol. 23(8), 1386–1388.

Miyake, et al., *Agric. Biol. Chem.* 1988, vol. 52(7), 1649–1654.

Ashihara, et al., *Journal of Clincal Laboratory Analysis* 1987, vol. 1, 77–79.

*Primary Examiner*—Dian C. Jacobson
*Attorney, Agent, or Firm*—Theodore J. Leitereg

[57] ABSTRACT

A method for determining the presence of an analyte which is a specific binding pair member in a sample suspected of containing the analyte is described. The method involves: bringing together in an aqueous medium, the sample, an enzyme bound to a first specific binding pair member and an inhibitor for the enzyme bound to a second specific binding pair member wherein each specific binding pair member is capable of binding to the analyte or to a specific binding pair member complementary to the analyte; analyzing the medium for the activity of said enzyme; and relating the activity to the amount of analyte present in the medium. Compositions of matter and kits are also described.

27 Claims, No Drawings

HOMOGENEOUS IMMUNOASSAYS USING ENZYME INHIBITORS

BACKGROUND OF THE INVENTION

1. Field of the Invention

Enzyme immunoassays are a very important tool in diagnostics and have several advantages, particularly over radioimmunoassays including, for example, the avoidance of radiation hazards, the convenience of detecting a chromogenic response, the avoidance of reagent instability due to radioactive decay, and the opportunity to amplify the response due to the ability of enzymes to generate many molecules of product per molecule of enzyme.

Enzyme immunoassays operate upon the principle that enzymes are biological catalysts that accelerate specific chemical reactions. Since a single molecule of catalyst can transform many molecules of substrate to product by repeating the catalytic reaction, the catalyst acts as an amplifier. Enzymes are therefore easily detectable at very low concentrations. This sensitivity makes enzymes useful as immunochemical labels. In an enzyme immunoassay for an analyte in a sample, an appropriate enzyme that is conjugated to one of the immunoreactants becomes bound to another immunoreactant or to the analyte and the activity of the enzyme is determined by measuring the conversion of an enzyme substrate to a product. The amount of product is an indication of the amount of analyte in the sample.

In heterogeneous enzyme immunoassays such as an ELISA assay, the unbound enzyme is first separated from the bound enzyme before measuring the enzyme activity.

Other assays, known as homogeneous enzyme immunoassays, detect the amount of enzyme activity as an indication of the amount of analyte, without the need to separate unbound enzyme from enzyme that is bound to an immunoreactant. These assays use an enzyme whose activity is capable of being modulated as a result of binding to the immunoreactant. One such method uses an enzyme-labeled ligand and a receptor, where the enzyme activity changes when the receptor is bound to an analyte instead of to the enzyme. Another such method involves using an enzyme-labeled receptor and measuring a change in enzyme activity upon binding of the receptor to a ligand. Another method, known as an enzyme channeling immunoassay, depends on a change in the enzyme activity when two enzymes are caused to come into close proximity with each other as a result of immunochemical binding. The enzymes are related in that the product of one enzyme is a substrate for the other. An excellent overview of enzyme immunoassays is presented in "Enzyme-Immunoassay", Edward T. Maggio, ed., CRC Press, Inc. (1980).

In homogeneous enzyme immunoassay methods, it is often difficult to adequately modulate the activity of an enzyme reagent with an antibody and some enzymes provide little or no modulation. The present invention provides an improvement in homogenous enzyme immunoassays wherein it is possible to modulate the activity of enzymes that heretofore have not been useful in enzyme immunoassays and thereby increase the versatility and sensitivity of the homogeneous enzyme immunoassay method.

2. Description of the Related Art

Anti-enzyme antibodies have been described as enzyme activity modulators. In Ngo, et al., *FEBS Letters* 116(2):285–288 (1980), an enzyme modulator is covalently linked to a ligand that is similar to the analyte such that the amount of modulator free to regulate enzyme activity is dependent upon the amount of analyte present. For example, ligand that has been labeled with anti-horseradish peroxidase (HRP) antibodies competes with analyte for binding to anti-analyte antibodies. Upon addition of HRP, any ligand-labeled anti-HRP antibodies remaining become bound to HRP, making it enzymatically inactive.

In U.S. Pat. No. 4,686,181, anti-enzyme antibodies are used to inhibit the activity of glucose-6-phosphate dehydrogenase (G6PDH). Anti-G6PDH is conjugated to the analyte or an analog of the analyte. A liquid medium containing the analyte is combined with a binding agent for the analyte, the anti-G6PDH-conjugate, and G6PDH. G6PDH activity is then measured. Skold, et al., *Journal of Immunology* 138 (10):3408–3414 (1987) also describes use of anti-G6PDH antibodies to modulate G6PDH activity.

IgG antibodies have also been described as enzyme activity modulators. Wei, et al., *Clin. Chem.* 23(8): 1386–1388 (1977) describes inhibition of enzymatic activity by IgG. When IgG binds to anti-IgG antibodies labeled with phospholipase C, the phospholipase C activity is suppressed. The catalytic site of the enzyme is presumably masked, which prevents its interaction with substrate.

Hybrid antibodies have been described as enzyme modulators. In Ashihara, et al., *Journal of Clinical Laboratory Analysis* 1:77–79 (1987), hybrid antibodies are described that are capable of binding to antigen or enzyme competitively and of inhibiting enzyme activity.

Chemical compounds have also been used to modify enzyme activity. United Kingdom Patent No. 1,595,101 describes an enzyme modifier immunoassay using a modifier, which is bound to a ligand or to a receptor for the ligand. The assay involves forming a complex between the modifier labeled member and the analyte, followed by addition of enzyme and substrate to the assay mixture, and measurement of enzyme activity. Miyake, et al., *Agric. Biol. Chem.* 52(7):1649–1654 (1988) describes several compounds capable of inhibiting the enzyme activity of β-galactosidase.

Inhibitors, either anti-enzyme antibodies or chemical compounds, have been used to reduce enzyme activity. EPO No. 0,272,691 describes an assay where antibody or antigen bound to a solid phase is combined with a sample to be assayed and an enzyme-labeled antibody or antigen. An insoluble solid carrier bound to an enzyme inhibitor is added to the liquid remaining after the antigen-antibody interaction, to reduce the activity of the enzyme in the unreacted enzyme-labeled antibody or antigen present in the liquid.

SUMMARY OF THE INVENTION

The present invention involves a method for determining the presence of an analyte, which is a specific binding pair ("sbp") member, in a sample suspected of containing the analyte. The method involves: (a) bringing together in an aqueous medium, the sample, an enzyme bound to a first sbp member, and an inhibitor for the enzyme bound to a second sbp member, wherein the sbp members are each capable of binding to the analyte or to an sbp member complementary to the analyte; (b) analyzing the medium for enzyme activity; and (c) relating the activity to the amount of analyte present in the medium.

The invention also pertains to an improved immunoassay for determining the amount of an analyte in a sample, comprising the steps of: (a) forming a complex between two complementary sbp members, where the sbp members are a ligand and a receptor, in a medium; (b) analyzing the medium to detect the amount of the complex; and (c) relating the amount of the complex to the amount of analyte in the sample. The improvement comprises using an enzyme bound to one of the sbp members and an inhibitor for the enzyme bound to the other sbp member.

The invention further concerns an immunoassay for determining the presence of an analyte in a sample suspected of containing the analyte, where (1) the sample, (2) a first conjugate of an enzyme with an analyte analog, and (3) a second conjugate of an inhibitor for the enzyme with an antibody to the analyte are brought together in an aqueous medium. Binding of the second conjugate to the first conjugate is modulated by the presence of analyte in the medium. The enzymatic activity of the medium is then determined.

The invention also concerns compositions of matter. One composition of matter of this invention is a solution of a first specific binding pair member, for example an antigen, bound to an enzyme and a second sbp member, for example an antibody, bound to an inhibitor for the enzyme. Another composition of the invention is a solution of a drug having a molecular weight of less than 2000 covalently bound to an enzyme and an antibody to the drug covalently bound to an inhibitor, usually a competitive inhibitor, for the enzyme. Still another composition of the invention is a solution of a drug having a molecular weight of less than 2000 bound to β-galactosidase, and an antibody to the drug bound to an inhibitor, usually a competitive inhibitor, for β-galactosidase.

The invention further pertains to a kit for carrying out an immunoassay for an analyte which, in packaged form, has a first conjugate of a first sbp member with an enzyme and a second conjugate of a second sbp member with an inhibitor for the enzyme.

The invention also concerns a conjugate of an immunoglobulin with an inhibitor, such as a competitive inhibitor, of β-galactosidase, where the conjugate binds to β-galactosidase in the absence of enzyme substrates with a dissociation constant of $10^{-2}$ to $10^{-8}$ M.

The invention also pertains to novel compounds useful as inhibitors for β-galactosidase.

DESCRIPTION OF THE SPECIFIC EMBODIMENTS

Before proceeding further with the description of the specific embodiments of the present invention, a number of terms will be defined.

Analyte: the compound or composition to be measured, the material of interest, which is usually a member of a specific binding pair and may be a ligand, usually antigenic or haptenic, a single compound or plurality of compounds which share at least one common binding or determinant site, or a receptor. Ligand analytes are characterized by being monovalent or polyvalent, while receptor analytes may have a single or a plurality of binding sites.

The precise nature of the analytes together with numerous examples of analytes of interest are disclosed in U.S. Pat. No. 4,299,916, columns 16 to 23, and U.S. Pat. No. 4,275,149, columns 17 and 18, which disclosures are incorporated herein by reference.

Polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like. For the most part, polyvalent ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000, and among hormones of interest, about 5,000 to 60,000.

Monovalent ligand analytes will generally be from about 100 to 2,000 molecular weight, more usually from about 125 to 1,000. Analytes of interest include drugs, drug metabolites, pesticides, pollutants, and the like, an extensive listing of which is set forth in U.S. Pat. No. 4,806,488, column 3, which disclosure is incorporated herein by reference.

An extensive listing of useful ligands may be found in U.S. Pat. No. 4,275,149, the disclosure bridging columns 12 to 17, which disclosure is incorporated herein by reference.

For receptor analytes, the molecular weights will generally range from about 10,000 to $2 \times 10^8$, more usually from about 10,000 to $10^6$. For immunoglobulins, IgA, IgD, IgE, IgG and IgM, molecular weights will generally vary from about 160,000 to about $10^6$. Enzymes will normally vary from about 10,000 to 6,000,000 in molecular weight. Natural receptors vary widely, being generally at least about 25,000 molecular weight and may be $10^6$ and higher, and include such materials as avidin, thyroxine binding globulin, thyroxine binding prealbumin, transcortin, membrane surface proteins, etc.

Member of a specific binding pair ("sbp" member): one of two different molecules, having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. Other specific binding pairs which are not immunological pairs are also included in this invention, for example, biotin-avidin, hormones-hormone receptors, nucleic acid duplexes, IgG-protein A, DNA–DNA, DNA–RNA, and the like. Complementary sbp members bind to one another, as for example, a ligand and its complementary receptor. An sbp member is analogous to another sbp member if it is capable of binding to the same complementary sbp member and may be either a ligand or a receptor that has been modified by replacement of at least one hydrogen atom by a group to provide, for example, a labeled ligand or a labeled receptor. The sbp members can be analogous to or complementary to the analyte or to an sbp member complementary to the analyte.

Ligand: any organic compound for which a receptor naturally exists or can be prepared.

Antigen: any compound capable of binding to an antibody, or against which antibodies can be raised.

Receptor: any compound or composition capable of recognizing a particular spatial and polar organization of a molecule, e.g., epitopic, binding or determinant site. Illustrative receptors include naturally occurring receptors such as thyroxine binding globulin, antibodies, enzymes, Fab fragments, lectins, nucleic acids, protein A, complement component C1q, and the like.

Antibody: an immunoglobulin having an area on the surface or in a cavity that specifically binds to and is thereby defined as complementary with a particular spatial and polar organization of another molecule. The antibody can be monoclonal or polyclonal and can be prepared by techniques that are well known in the art such as immunizing a host and collecting sera (polyclonal) or by preparing continuous hybrid cell lines and collecting the secreted protein (monoclonal). Antibodies may include a complete immunoglobulin or fragment thereof, which immunoglobulins include the various classes and isotypes, such as IgA (IgA1 and IgA2), IgD, IgE, IgM, and IgG (IgG1, IgG2, IgG3 and IgG4), etc. Fragments thereof may include Fab, Fv and F(ab')$_2$, Fab', and the like.

Analyte analog or ligand analog: a modified analyte or analyte surrogate or modified ligand or ligand surrogate that can compete with the analyte or ligand for binding to a receptor, the modification providing means to join an analyte or ligand to another molecule. The analyte analog or ligand analog usually differs from the analyte or ligand by more than replacement of a hydrogen with a bond that links the analyte analog or ligand analog to a hub or label, but need not. The term analyte surrogate or ligand surrogate refers to a compound having the capability of specifically binding a receptor complementary to the analyte or ligand. Thus, the analyte surrogate or ligand surrogate can bind to the receptor in a manner similar to the analyte or ligand. The surrogate could be, for example, an antibody directed against the idiotype of an antibody to the analyte or ligand.

Inhibitor: a compound or group capable of reversibly binding to an enzyme and inhibiting the enzyme's activity, usually a competitive inhibitor. Complete inhibition is not necessary. Minimally, all that is required is that there be a measurable difference between completely uninhibited and maximally inhibited enzyme, which difference would allow for a qualitative detection of the analyte. However, normally the greater the difference in activity produced by the inhibitor, the more sensitive the assay, and the greater the precision in quantitative determination of analyte through a desired range of concentrations.

Reversible binding: normally binding that is noncovalent, and generally refers to binding between an enzyme and inhibitor where dissociation of the bound complex results in no overall chemical change in either component. Many reversible inhibitors are competitive inhibitors. Competitive inhibitors bind to an enzyme in competition with the enzyme substrate and thus bind less completely and inhibit less efficiently the greater the concentration of substrate.

Sample pretreatment: an optional step in an assay, designed to make the target analyte more readily available to one or more of the assay reagents or to reduce interference in the assay by sample components. Samples to be analyzed by the method of the present invention may be pretreated to: separate or lyse cells; precipitate, hydrolyse or denature proteins; hydrolyze lipids; solubilize analyte; or the like. Such pretreatment may include, without limitation: centrifugation; treatment of the sample with an organic solvent, for example, an alcohol, preferably an alcohol having less than about 7 carbon atoms such as methanol; and treatment with detergents, for example, sodium hydroxide.

An assay method of this invention comprises combining a sample suspected of containing an analyte, which is an sbp member, with at least two reagents: (1) an enzyme bound to a first sbp member and (2) an inhibitor for the enzyme bound to a second sbp member. The first and second sbp members are each capable of binding to the analyte or to an sbp member complementary to the analyte. The medium is then analyzed for the activity of the enzyme and the activity is related to the amount of analyte present in the medium. This invention finds particular utility in assays for drugs such as digoxin and cyclosporin.

This invention can utilize any enzyme whose activity is capable of being inhibited when it is reversibly bound by an inhibitor, where the inhibitor is bound to an sbp member.

Enzymes vary widely in their substrates, cofactors, specificity, ubiquitousness, temperature stability, optimum pH, turnover rate, and the like. Other than inherent factors, there are also the practical considerations in enzyme selection, such as the specific activity of the enzyme, the availability of substrates that are converted to readily detectable products, the stability of the enzyme, and whether the enzyme is commercially available.

From the standpoint of operability, a wide variety of enzymes can be used in this invention and an extensive list including substrates, cofactors and natural sources is provided in U.S. Pat. Nos. 3,817,837 and 4,203,802, the disclosures of which are incorporated herein by reference; *Enzyme Nomenclature*, Edwin C. Webb, ed., Academic Press, New York (1984) at pages 20–474; *Enzymes*, Malcolm Dixon, et al., Third Edition, Academic Press, New York (1979) at pages 683–972; *Enzyme Handbook*, Vol. I, II, and Supp. I, Thomas E. Barman, Springer-Verlag, New York (1969) at pages 23–499, 501–915, and 16–503 respectively; and *Enzyme Handbook*, Vol. 1 and 2, D. Schomburg and M. Salzmann, ed.s, Springer-Verlag, New York (1990). In brief, these include oxidoreductases, transferases, hydrolases, lyases, isomerases and ligases (synthetases).

As a practical matter, there will be a number of groups of enzymes which are preferred. Employing the International Union of Biochemists (I.U.B.) classification, the oxidoreductases (1.), hydrolases (3.) and lyases (4.) are of interest, with the oxidoreductases and hydrolases being preferred. Of the oxidoreductases, the ones acting on the CHOH group, the aldehyde or keto group, or the CH—NH$_2$ group as donors (1.1, 1.2 and 1.4, respectively) and those acting on hydrogen peroxide as acceptor (1.11) will be preferred. Also preferred are the oxidoreductases which employ nicotinamide adenine dinucleotide, or its phosphate or cytochrome as an acceptor, namely 1.x.1 and 1.x.2, respectively under the I.U.B. classification. Of the hydrolases, of particular interest are those acting on glycosyl compounds, particularly glycoside hydrolases, and those acting on ester bonds, both organic and inorganic esters, namely the 3.1 and 3.2 groups respectively, under the I.U.B. classification.

In choosing an enzyme for commercialization, as compared to a single or limited use for scientific investigation, there will be a number of desirable criteria. The enzyme should be stable when stored for a period of at least three months, and preferably at least six months at temperatures of −20° C. or above.

The enzyme should be readily detectable at concentrations equal or less than that of the analyte through measurement of disappearance of its substrate or formation of a product. Preferably, detection can be carried out under conditions that will not disrupt ligand-receptor binding, normally at pH 4–11, usually 6–9. Preferably, the enzyme will have an optimum pH for the turnover rate at or near the optimum pH for binding of the analyte to a complementary sbp member.

A product should be either formed or destroyed as a result of the enzyme reaction. Desirably, the product should absorb light in the ultraviolet region or the visible region, that is, the range of about 250–800 nm, preferably 400–700 nm. The substrate may either be the natural substrate, or a synthetically available substrate. Exemplary products and substrates for the various respective enzymes are set forth in *Enzymes*, supra.

Preferably, the enzyme employed, or other enzymes with like activity, will not be present in the fluid to be measured, or can be easily removed or deactivated prior to the addition of the assay reagents. Also, it is desirable to employ an enzyme for which there is no naturally occurring inhibitor in the fluid to be assayed.

For synthetic convenience, it will frequently be desirable to attach sbp members, particularly haptens, to amino groups of the enzyme. However, other groups may be bound to the sbp member including hydroxyl groups, thiols, phenols, imidazoles, carboxyl groups, etc.

Conjugation of proteins, including enzymes, to a wide variety of materials, such as drugs, proteins, polysaccharides, nucleic acids, and the like, has found extensive exemplification in the literature. A wide variety of linking groups and linking functionalities may be employed, and an extensive listing of linking groups is set out in U.S. Pat. No. 4,203,802, columns 37–43, which disclosure is incorporated herein by reference. Conveniently, oxocarbonyl, diazo, sulfonyl, oximino, imido, and thiono functionalities may be employed. With oxocarbonyl, reductive alkylation may be advantageously employed. The linking group between the functionalities may be a bond, but will more usually have at least one carbon atom, more usually at least two carbon atoms and may have as many as 50 or more atoms, other than hydrogen. Methods for conjugating enzymes to proteins may be found in U.S. Pat. Nos. 3,791,932 and 3,839,153, and methods for conjugating monoepitopic ligands, that is, haptens, may be found in U.S. Pat. No. 3,817,837, particularly at columns 31–34 and in the working examples, which disclosures are incorporated herein by reference.

An enzyme molecule must have at least one molecule of the sbp member bound to it and preferably at least as many sbp members as there are catalytic sites, more preferably, at least three molecules of the sbp member bound per catalytic site. Generally there will be about 1 to 10 sbp member molecules per binding site of the enzyme. As used herein the term "catalytic site" means the active site of the enzyme where catalysis of the conversion of substrate to product takes place, and the term "molecule" includes both a molecule or a residue of a molecule. The enzyme may be covalently or non-covalently bound to the sbp member, preferably covalently bound. When non-covalently bound, the enzyme will normally be bound to a receptor for the enzyme.

The inhibitor reversibly binds to the enzyme and modulates, preferably inhibits, the enzyme's activity. Reversible binding means that at least a portion of the inhibitor that binds to the enzyme is capable of dissociating from the enzyme without a net chemical change. The following examples are merely illustrative of enzyme inhibitors useful in the invention, and are not intended to be limiting.

In one embodiment of the invention, the inhibitor is structurally similar to the substrate, transition state, or product, and will compete for binding to the enzyme. Such competition from the inhibitor will interfere with substrate binding to the enzyme, resulting in attenuation of the enzyme's activity.

In another embodiment, the inhibitor binds to an effector site that affects the activity of the enzyme, so that upon such binding of the inhibitor to the enzyme, the catalytic properties of the enzyme are reduced.

In still another embodiment, the inhibitor is cofactor-like in structure and competes with the cofactor for binding to the enzyme.

In yet another embodiment, the inhibitor is a receptor such as an antibody for the enzyme that upon binding to the enzyme, changes the enzyme's conformation or sterically blocks substrate access to the active site.

Preferred inhibitors have molecular weights of less than 2000. The inhibitors may be covalently conjugated directly to an sbp member as described above with reference to the conjugation of the enzyme to an sbp member, or a number of inhibitors may be conjugated to a hub molecule that is covalently or non-covalently bound to an sbp member. The hub molecule may be a natural or synthetic polymer such as dextran, polyacrylate, protein, polysaccharide, oligonucleotide, etc. Alternatively, the inhibitor may be bound non-covalently to the sbp member, in which case the inhibitor will normally be bound to a receptor for the sbp member.

Generally, at least about one molecule of the inhibitor is bound per binding site of the sbp member to which it is conjugated and frequently there will be at least three or more molecules of the inhibitor bound per binding sit e of the sbp member. In general, it is desirable to bind as many inhibitors as possible without compromising the binding ability or stability of the sbp member. Usually, about 6 to 10 or more molecules of inhibitor are bound per binding site of the sbp member. As used herein the term "binding site" means the site of the sbp member where binding to its complementary sbp member occurs. Usually, the sbp member to which the inhibitor is bound will have a molecular weight of at least 10,000, although conjugates of inhibitors with low molecular weight sbp members such as haptens of molecular weight less than 2000 are also within the scope of this invention.

The inhibitor, when bound to an sbp member, preferably binds to the enzyme with a dissociation constant in the range of $10^{-2}$ to $10^{-8}$ M, usually in the range of $10^{-3}$ to $10^{-8}$ M, when the sbp member bound to the inhibitor is not otherwise bound to the enzyme. In this situation the term "not otherwise bound" means that the sbp member bound to the inhibitor is not bound to the enzyme or to an sbp member bound to the enzyme. For example, where the enzyme is covalently labeled with a drug and an antibody to the drug is covalently labeled with an inhibitor of the enzyme, the antibody is not otherwise bound to the drug on the enzyme when an excess of free drug capable of binding to the antibody is included in the medium containing the two conjugates. Normally, an excess of drug implies at least five-fold, usually at least ten-fold more free drug than drug bound to the enzyme.

It is contemplated that any enzyme-inhibitor pair can be used in this invention. Such pairs include by way of example and not limitation: the enzyme glucose-6-phosphate dehydrogenase and, for example, the inhibitor coenzyme A; the enzyme acetylcholinesterase and, for example, the inhibitor decamethonium bromide, having the structure:

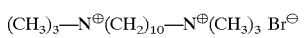

and the enzyme horseradish peroxidase and, for example, the inhibitor benzoylhydroxamic acid.

Of particular interest in the present invention is the use of the enzyme β-galactosidase. The activity of β-galactosidase-antigen conjugates is poorly modulated by anti-antigen antibodies when low molecular weight substrates are used. Although the modulation can be increased if the substrates are attached to a macromolecular support, the assays using the resulting large substrates have been associated with interference caused by anti-β-galactosidase antibodies in serum. Nonetheless, because β-galactosidase can be detected with high sensitivity in serum with minimal interference from serum components, it is a desirable enzyme to utilize in an assay. Thus, a preferred embodiment of this invention contemplates, for example, a conjugate of an antibody, preferably an intact immunoglobulin, with an inhibitor of β-galactosidase and a conjugate of β-galactosidase with an analyte analog, which is complementary to the antibody. The inhibitor can be a competitive inhibitor. The dissociation constant for binding of the inhibitor conjugate to enzyme in the absence of enzyme substrates, the inhibition constant $K_i$, will normally be in the range of $10^{-2}$ to $10^{-8}$ M, preferably $10^{-3}$ to $10^{-8}$ M, when the antibody is substantially not otherwise bound to the analyte analog.

Common inhibitors of β-galactosidase include compounds selected from the group consisting of multiply hydroxylated piperidines and multiply hydroxylated pyrans.

One group of inhibitors are thiogalactosides having the structure:

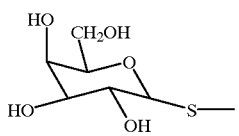

These inhibitors may be attached to an sbp member by means of an attaching group bound to S, of from 1–50 atoms, other than hydrogen, containing a functional group for attachment to an sbp member such as hydroxy, carboxyl, halide, amino, maleimido group, sulfonic acid, etc. These inhibitors can in general be synthesized by reaction of a mercaptan, eg. ω-mercaptocaproic acid, with a protected 1-halogalactoside, such as tetra-acetyl-1-chlorogalactoside.

A second group of inhibitors are derived from 1-deoxygalactostatin, a known inhibitor of β-galactosidase that has the following structure:

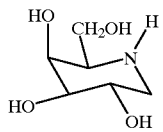

The derived β-galactosidase inhibitors have the following structure:

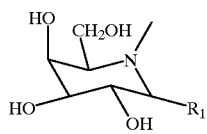

where $R_1$ is selected from the group consisting of hydrogen and hydroxyl (—OH). These inhibitors may be attached to an sbp member by means of an attaching group bound to N, of from 1–50 atoms, other than hydrogen, containing a functional group for attachment to an sbp member such as hydroxy, carboxyl, halide, amino, maleimido group, sulfonic acid, etc. These inhibitors for β-galactosidase can, in general, be synthesized by alkylation of 1-deoxygalactostatin, for example with an ω-haloacid.

Thiogalactosides and galactostatin-derived inhibitors can be readily coupled to specific binding pair members for use in the invention. For example, the N-hydroxysuccinimide (NHS) ester of an inhibitor having a carboxyl in its attaching group can be coupled with antibody amino groups, or inhibitors having a maleimido group can be coupled with sulfhydryl groups that have been introduced onto the antibody to facilitate such coupling.

The resulting inhibitor-antibody conjugate may be employed in an assay for an antigen that is complementary to the antibody. For example, an antibody to a tetrahydrocannabinol (THC) derivative conjugated to the inhibitor can be used with a conjugate of β-galactosidase with the THC derivative in an assay for THC or its metabolites. In the assay, the sample and the antibody conjugate will preferably be combined first, followed by addition of the enzyme conjugate and a chromogenic enzyme substrate such as o-nitrophenol-β-galactoside, although other orders of addition can sometimes be used. After incubation for a time sufficient for a measurable amount of product to be formed, the amount of product is determined in relation to the amount of analyte in the sample.

The assay for the analyte will normally be carried out in an aqueous buffered medium at a moderate pH, generally that which provides optimum assay sensitivity.

The aqueous medium may be solely water or may include from 0.01 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members of specific binding pairs and the enzyme and inhibitor and the pH optimum for detection of enzyme activity.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50°, more usually from about 15° to 40° C.

The concentration of analyte which may be assayed will generally vary from about $10^{-4}$ to $10^{-15}$ M, more usually from about $10^{-6}$ to $10^{-13}$ M. Considerations, such as whether the assay is qualitative, semi-quantitative or quantitative (relative to the amount of analyte present in the sample), the particular detection technique and the concentration of the analyte will normally determine the concentrations of the various reagents.

While the concentrations of the various reagents comprising sbp members in the assay medium will generally be determined by the concentration range of interest of analyte, the final concentration of each of these reagents will normally be determined empirically to optimize the sensitivity of the assay over the range. That is, a variation in concentration of analyte which is of significance should provide an accurately measurable signal difference. The concentration of the enzyme substrate will be selected to maximize the response of the assay and will usually be at least as high as the $K_m$ of the enzyme and preferably 2 to 10 times $K_m$.

While the order of addition may be varied widely, there will be certain preferences depending on the nature of the assay. The simplest order of addition is to add all the materials simultaneously and determine the effect that the assay medium has on the signal as in a typical homogeneous assay. Preferably, the reagents will be combined sequentially, usually sample and inhibitor being combined prior to addition of the enzyme and substrate. Optionally, an incubation step may be involved following one or more of the additions, generally ranging from about 5 seconds to 3 hours, more usually from about 30 seconds to 30 minutes. After all of the reagents have been combined either simultaneously or sequentially, the signal is determined. The signal is related to the amount of analyte in the sample tested.

In one embodiment of the invention, the analyte in the sample and an analyte analog-enzyme conjugate compete for sites on an antibody for the analyte, resulting in inhibitor-antibody:analyte and inhibitor-antibody:analyte analog-enzyme complexes. A substrate for the enzyme is then added. The enzyme in the inhibitor-antibody:analyte analog-enzyme complex can only inefficiently catalyze the conversion of substrate to product due to the presence of inhibitor. However, the enzyme in any unbound analyte analog-enzyme conjugate retains its original catalytic activity. The enzyme catalyzed reaction results in the formation of a detectable product that may, for example, be chromophoric, luminescent, fluorescent, electro-luminescent, or the like. The enzyme activity in the medium is then determined, usually by spectrophotometric means, and is compared to the enzyme activity determined when a calibrator or reference sample is tested in which a known amount of the analyte is present. Typically, the calibrator or reference sample is tested in a manner substantially the same as the sample suspected of containing analyte. Frequently, a comparison can be made of the result from an unknown sample with the results of the assay of several standard samples. The standard samples will typically contain differing, but known, concentrations of the analyte to be determined. Preferably, the concentration ranges present in the standard samples will span the range of suspected analyte concentrations in the unknown samples.

An example of a non-competitive assay is a sandwich assay involving two antibodies, one of which is labeled with an enzyme and one with a reversible inhibitor of the enzyme. Usually, the two antibodies are combined with the sample in an aqueous medium, the mixture is incubated for 5 seconds to 30 minutes, and the enzyme substrate is then added. The rate of product formation is then measured and related to the amount of analyte in the sample by reference to the rate obtained using a calibrator solution in place of the sample.

There are numerous ways in which the present invention can be practiced and the following examples are merely illustrative and not limiting.

One method of practicing the invention where the analyte in a sample is a ligand or receptor, involves one reagent (Ez-L) which can be an enzyme (Ez) bound to a ligand analog (L). The second reagent (R-I) can be an inhibitor (I) for the enzyme bound to a receptor for the ligand (R). Depending upon whether the analyte is a ligand or a receptor, it can bind to R-I or Ez-L respectively and thereby compete with Ez-L for binding to the R-I conjugate, or vice versa. The reagents can be added to the sample in a liquid medium, either sequentially or simultaneously. The following complex, in which the enzyme activity is attenuated, is formed in an amount that is inversely related to the amount of the analyte in the sample:

Ez-L:R-I

The total activity of the medium is then related to the amount of analyte in the sample. Alternatively, the reagents can be an enzyme bound to a receptor (Ez-R) and an inhibitor bound to a ligand (L-I), forming in the assay the complex:

Ez-R:L-I in which enzyme activity is likewise attenuated and which is found in an amount that is inversely related to the amount of analyte in the sample.

In another method of practicing the invention where the analyte in a sample is a multiepitopic ligand (L), one reagent can be an enzyme (Ez) bound to a first antibody for the ligand ($Ab_1$). The second reagent can be an inhibitor (I) for the enzyme bound to a second antibody for the ligand ($Ab_2$) that binds to a different epitope than the first antibody. The reagents can be either combined sequentially or simultaneously in an aqueous medium with the sample. This non-competitive assay would yield the complex:

Ez-$Ab_1$:L:$Ab_2$-I in which the enzyme activity is attenuated. The enzyme activity of the medium is directly related to the amount of analyte in the sample.

In yet another method of practicing the invention where the analyte in a sample is a ligand or receptor, one reagent can be an enzyme (Ez) bound to a ligand analog (L) and a second reagent can be a receptor for the ligand (R), where one of the members of the ligand-receptor pair can bind to the analyte. A third reagent can be an inhibitor (I) for the enzyme bound to an sbp member (sbp) complementary to the receptor. Analyte competes with the binding of the Ez-L conjugate to the receptor and the receptor is bound to the sbp-I conjugate. The reagents can be added to an aqueous medium containing the sample either sequentially or simultaneously. In the absence of analyte, the complex Ez-L:R:sbp-I is formed, in which enzyme activity has been attenuated. Thus, in proportion to the amount of analyte present, there will be increasing amounts of unbound enzyme and the activity of the enzyme measured following mixing of the reagents will be correspondingly increased.

Alteratively, the first reagent can be the Ez-L conjugate described above, the second reagent can be a receptor for the ligand bound to a first sbp member ($sbp_1$) and the third reagent can be an inhibitor bound to an sbp member ($sbp_2$) which is complementary to the first sbp member ($sbp_1$), yielding the complex:

Ez-L: R-$sbp_1$:$sbp_2$-I

In this latter example, preferably $sbp_1$ or $sbp_2$ is a small molecule or a residue of a small molecule, having a molecular weight of from 100 to 2000, preferably 150 to 1000, for which a receptor exists or can be prepared. Examples of such small molecules include derivatives of biotin, lysergic acid, fluorescein and vitamin $B_{12}$, when the corresponding receptors are avidin, anti-lysergic acid, anti-fluorescein and intrinsic factor, respectively.

In still yet another method of practicing the invention where the analyte in a sample is a ligand or receptor, one reagent can be an enzyme (Ez) bound to a first sbp member ($sbp_1$) and a second reagent can be a second sbp member ($sbp_2$) bound to a ligand analog (L), where $sbp_2$ is complementary to $sbp_1$. A third reagent can be an inhibitor (I) for the enzyme bound to a receptor for the ligand (R), where one of the members of the ligand-receptor pair can bind to the analyte. Analyte competes with the binding of the $spb_2$-L conjugate to the receptor and the $spb_2$-L conjugate is bound to the Ez-$sbp_1$ conjugate. The reagents can be added to an aqueous medium containing the sample, either sequentially or simultaneously. In the absence of analyte, the complex Ez-$sbp_1$:$sbp_2$-L:R-I is formed, in which enzyme activity has been attenuated. Thus, in proportion to the amount of analyte present, there will be increasing amounts of unbound enzyme and the activity of the enzyme measured following mixing of the reagents will be correspondingly increased. The sbp members are preferably small molecules as defined above.

Another embodiment of this invention involves an assay for determining the presence of an analyte in a sample suspected of containing the analyte, which comprises: bringing together in an aqueous medium, the sample, a first conjugate of an enzyme with an analyte analog and a second conjugate of an inhibitor for the enzyme with an antibody to the analyte wherein binding of the second conjugate to the first conjugate is modulated by the presence of analyte in the medium; and determining the enzymatic activity of the medium.

This invention also contemplates compositions of matter. One composition comprises a solution of an antigen bound to an enzyme and an antibody for the antigen bound to a reversible inhibitor for the enzyme. Another composition comprises a solution of a drug of molecular weight less than 2000 covalently bound to an enzyme and an antibody to the drug covalently bound to an inhibitor, usually a competitive inhibitor, for the enzyme. Another composition in accordance with the invention comprises a solution of a drug of molecular weight less than 2000 bound to β-galactosidase, and an antibody to the drug bound to an inhibitor, usually a competitive inhibitor, for β-galactosidase. Another composition comprises a conjugate of an immunoglobulin with an inhibitor, usually a competitive inhibitor, of β-galactosidase where the conjugate binds β-galactosidase with a dissociation constant in the range of $10^{-2}$ to $10^{-8}$ M, preferably in the range of $10^{-3}$ to $10^{-8}$ M, in the absence of enzyme substrate.

This invention also includes kits for carrying out an immunoassay for an analyte comprising in packaged form a first reagent comprising a conjugate of a first sbp member with an enzyme and a second reagent comprising a conjugate of a second sbp member with an inhibitor for the enzyme. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. As a matter of convenience, the reagents employed in the present invention can be provided in predetermined amounts. The reagents will include the sbp member-enzyme and sbp member-inhibitor conjugates as disclosed above, and can further include other packaged reagents for conducting an assay including members of the signal producing system, such as the enzyme substrate and any cofactor, calibrators, ancillary reagents, and so forth.

The relative amounts of the various reagents may be varied widely, to provide for concentrations in solution of reagents, which substantially optimize the sensitivity of the assay. The reagents may be provided as dry powders, usually lyophilized, including excipients, which on dissolution will provide for a reagent solution having the appropriate concentrations for performing the assay.

One kit contemplated by this invention comprises an antigen bound to an enzyme as one reagent and an antibody for the antigen bound to a reversible inhibitor for the enzyme as a second reagent. Another kit comprises a drug of molecular weight less than 2000 covalently bound to an enzyme as one reagent and an antibody to the drug covalently bound to an inhibitor, usually a competitive inhibitor, for the enzyme as a second reagent. Another kit in accordance with the invention comprises a drug of molecular weight less than 2000 bound to β-galactosidase as one reagent and an antibody to the drug bound to an inhibitor for β-galactosidase as a second reagent. Another kit comprises a reagent comprising a conjugate of an immunoglobulin with an inhibitor of β-galactosidase where the conjugate binds the β-galactosidase with a dissociation constant in the range of $10^{-2}$ to $10^{-8}$ M, in the absence of enzyme substrate.

The patents and patent applications referred to in the above description are each incorporated herein by reference in their entirety.

EXAMPLES

The invention is demonstrated further by the following examples, which are offered by way of illustration and not by way of limitation. All temperatures not otherwise indicated are in centigrade. All percents and parts not otherwise indicated are by weight, except for mixtures of liquids which are by volume. Unless otherwise indicated, materials employed in the various reactions are commercially available. The following abbreviations have the meaning indicated:

AcOH—acetic acid
BMW—butanol:MeOH:toluene:$H_2O$, 2:1.25:1:1
DCC—1,3-dicyclohexylcarbodiimide
DMF—dimethylformamide
DMSO—dimethyl sulfoxide
DTE—dithioerythritol
EDAC—1-(3-dimethylaminopropyl)-3-ethylcarbodiimide hydrochloride
EDTA—ethylenediaminetetraacetic acid
EGTA—ethylene glycol-bis(β-aminoethyl ether) N,N,N',N'-tetraacetic acid
EtOH—ethanol
$Et_2O$—diethyl ether
$Et_3N$—triethylamine
$Et_3SiH$—triethylsilane
IPTG—isopropyl-β-D-thiogalactopyranoside
MeOH—methanol
MES—2-(N-morpholino) ethane sulfonic acid
NHS—N-hydroxy succinimide
ONPG—o-nitrophenyl galactoside
PTLC—preparative TLC
$R_f$—retention coefficient
tBoc—t-butoxycarbonyl
TFA—trifluoroacetic acid
TLC—thin layer chromatography
TMS—trimethylsilyl Example 1

Preparation Of Amine-Reactive Deoxygalactostatin Inhibitor

The preparation of amine-reactive deoxygalactostatin inhibitor (3) is outlined as follows:

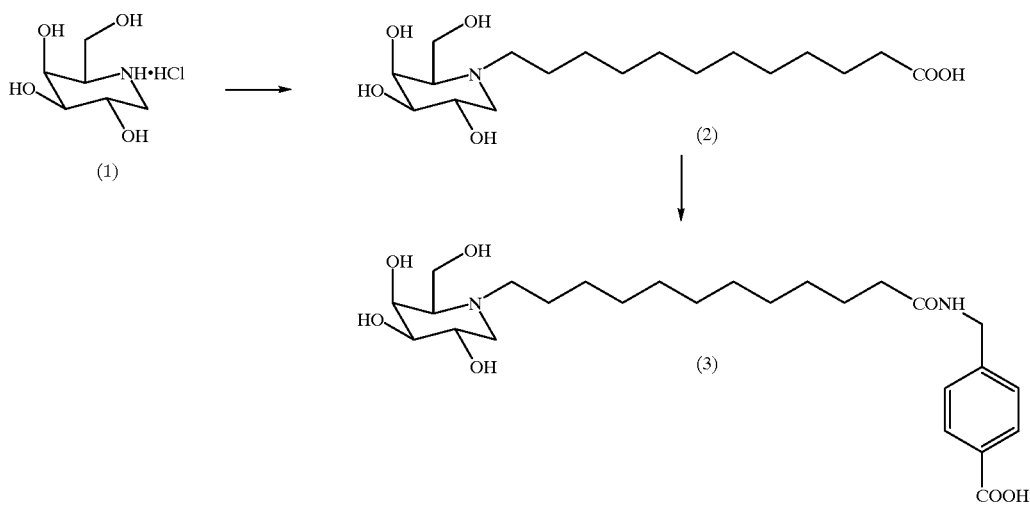

1-Bromododecanoic acid (600 mg, 2.1 mmol) and $K_2CO_3$ (~250 mg) were added to a solution of 1-deoxygalactostatin (1) (100 mg, 0.5 mmol) (See R. C. Bernotas, et al., *Carbohydrate Research,* 167:305 (1987)) in acetone:water (6:4, 15 ml) to adjust the pH to 8–9. After addition of NaI (few crystals) the reaction mixture was heated to 55° C. under argon for 48 hours. The resulting milky suspension was concentrated and centrifuged. The supernatant was loaded onto a Biorad AG 1-x-4 (OH⁻) (12×2 cm) and washed with $H_2O$ (500 ml) to recuperate starting material (25 mg, 25%). Product (2) was eluted with AcOH (200 ml, 2 M) as a pure compound. Yield: 75 mg, 40%.

N-hydroxysuccinimide (150 mg) and EDAC (150 mg) were added to a solution of compound (2) (120 mg) in DMF (10 ml). The reaction mixture was stirred overnight under argon and then added to a suspension of 4-(aminomethyl) benzoic acid (400 mg) in triethylamine (800 μl) and DMF (10 ml). After 0.5 hours the reaction was completed, the mixture was acidified with 0.1 N HCl and evaporated to dryness. The amine-reactive deoxygalatostatin inhibitor (3) was purified by preparative TLC (eluant:BMW). Extraction of the band corresponding to the product was done with MeOH followed by ethanol. Yield: 78 mg.

Example 2

Preparation Of Thiol-Reactive Deoxygalactostatin Inhibitor

The preparation of thiol-reactive deoxygalactostatin inhibitor (6) is outlined as follows:

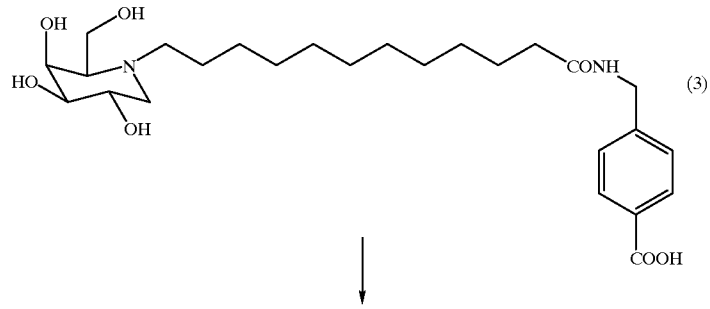

-continued

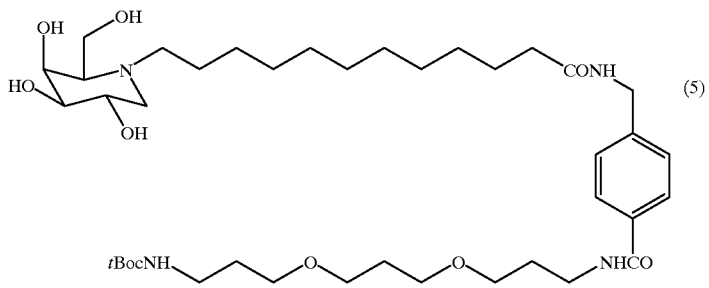

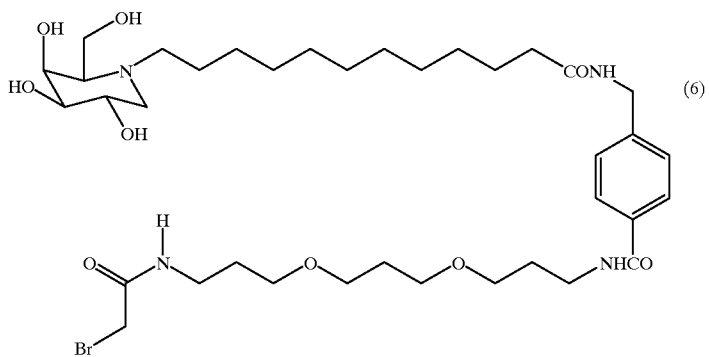

Dioxadodecanediamine was mono t-butyloxycarboxylated according to the procedure reported for 1,6-hexane diamine in J. B. Hansen, et al., *Synthesis* 404 (1982).

Compound (3) (25 mg) in DMF (4 ml) was treated with NHS (27 mg) and EDAC (110 mg) for 16 hours at room temperature under argon. The resulting mixture was added to a solution of amine (4) (76 mg):

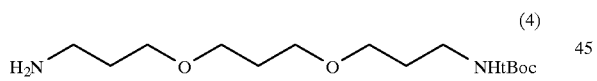

in DMF (250 μl) containing triethylamine (27 μl). After 30 minutes the reaction mixture was neutralized with HCl (0.1 N) and evaporated to dryness and the product was purified by preparative TLC (eluant:BMW). Extraction of major band with MeOH then EtOH gave the desired product (5). Yield: 18 mg.

Compound (5) (14 mg) was treated with TFA (0.5 ml) for 15 minutes. Then methanol was added and the solution was evaporated to dryness. The residue was dissolved in DMF (1 ml) and basified with Et$_3$N to pH 8–9. Bromoacetic acid-NHS ester (9 mg) was added, the mixture kept under argon for 1 hour, and then evaporated to dryness. Product (6) was purified by preparative TLC (eluant:BMW). Yield: 8 mg.

Example 3

Preparation Of Amine-Reactive Thiogalactoside Inhibitor

The preparation of the amine-reactive thiogalactoside inhibitor (11) is outlined as follows:

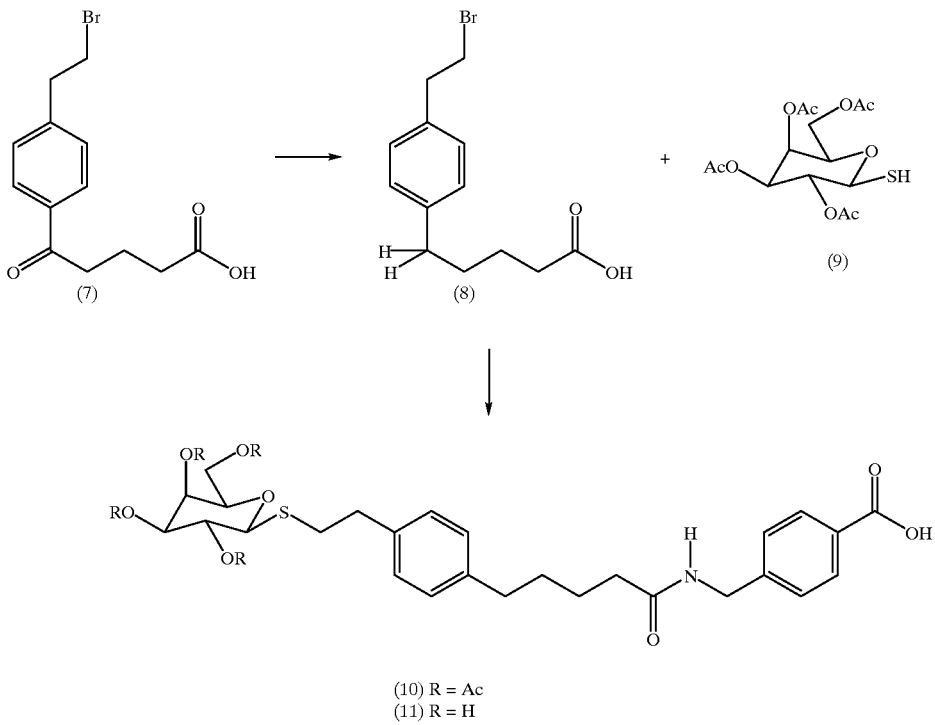

(10) R = Ac
(11) R = H

Phenylethylbromide (370 μl, 2.7 mmol) and glutaric anhydride (615 mg, 5.39 mmol) were cooled to ice-bath temperature in $CH_2Cl_2$ (20 ml) under argon. Aluminum dichloride (1.4 g) was added and the bath removed after 1 minute. The solution became red (passing from yellow to orange) after 30 minutes. $H_2O$ (50 ml) was added and the pH was dropped to pH 2–3 with 1 N HCl. The reddish color disappeared and the mixture was extracted with $CH_2Cl_2$ (3×100 ml). The combined organics were then extracted with aqueous $NaHCO_3$ (3×100 ml) and the aqueous extracts were acidified to pH 2 with 1 N HCl. Extraction with $CH_2Cl_2$ (3×50 ml), drying ($MgSO_4$) and evaporation of the solvent left an orange residue that was subjected to preparative TLC (4% MeOH-$CH_2Cl_2$, AcOH/30 drops per 200 ml) which gave pure product (7). Yield: 605 mg.

$Et_3SiH$ (133 μl, 0.835 mmol) was added to a solution of bromide (7) (100 mg) in TFA (254 μl, 3.3 mmol). After 18 hours at room temperature, methanol was added and the reaction mixture was evaporated to dryness. Crystallization from $CH_2Cl_2$—$Et_2O$-hexane gave pure compound (8). Yield: 80 mg.

$H_2O$ (3 ml) and $K_2CO_3$ (144 mg) were added to a solution of 2,3,4,6-tetra-O-acetyl-1-thio-β-D-galactopyranose (9) (See M. Cerny, et al., Monatsh. 94:290 (1963)) (178 mg) and (8) (100 mg) in acetone (5 ml). After 3 hours, $H_2O$ (20 ml) was added and the solution acidified to pH 2 with 1 N HCl. After evaporation of acetone, the mixture was extracted with $CH_2Cl_2$ (5×20 ml). The combined organics were dried ($Na_2SO_4$) and evaporated to dryness. Without further purification, the residue was dissolved in DMF (5 ml) and treated with NHS (120 mg, 1.05 mmol) and EDAC (267 mg, 1.4 mmol) for 18 hours. The mixture was then added to a suspension of 4-(aminomethyl)benzoic acid (370 mg) in DMF (2 ml) containing $Et_3N$ (600 Al). After 30 minutes, $H_2O$ (50 ml) was added, the mixture was then acidified to pH 2 with 1 N HCl, and extracted with $Et_2O$ (5×50 ml). The combined organics were washed with brine, dried ($Na_2SO_4$) and evaporated to dryness. Compound (10) was purified by preparative TLC (2% MeOH-$CH_2Cl_2$, AcOH/30 drops per 200 ml). Yield: 147 mg.

Compound (10) (100 mg) was dissolved in MeOH (10 ml) and MeONa (38 mg) was added. After 30 minutes, Amberlite IRC 50 ($H^+$) was added until the reaction mixture became neutral. The mixture was then filtered, and the resin washed with MeOH. The combined washings were concentrated and compound (11) was precipitated by addition of $CH_2Cl_2$. Yield: 60 mg.

Example 4

Purification Of Polyclonal Anti-Digoxin Antibody (R1273)

An Affigel-ouabain column, (4cm×2cm; 15 ml gel) was equilibrated with buffer (0.02 M Na phosphate, 0.15 M NaCl, pH 7.3). Crude R1273 (35 ml) was added and the eluant was passed 3 times over the column, which was then washed with buffer A (200 ml). The polyclonal antibody was then eluted with a solution of ouabain 10 mg/ml in the same buffer and 23 fractions were collected. Fractions 3–13 showed to be identical by gel electrophoresis and were pooled (42 ml) and used for the conjugation experiment. Fractions 14–22 (40 ml) were kept aside.

Example 5

Reduction And Alkylation Of Purified Polyclonal Anti-Digoxin Antibody (R1273)

A solution of the affinity purified R1273 antibody (2.35 mg/ml, 10 ml) had the pH adjusted to 8 with a $Na_2HPO_4$ solution (0.2 M) and EDTA (38 mg) was added. After 2 hours under argon, DTE (15 mg) was added and the reaction mixture was kept under argon for 5 hours. Then iodoacetamide (55 mg) was added and after another hour the reaction was dialyzed against buffer (4×2.5 l; 0.1 M sodium phosphate, 0.2 M sodium chloride, pH 8). The reduced and alkylated antibody R1273 was stored in the cold room until further usage.

Example 6

Random Labeling Of Anti-Digoxin Antibody With Inhibitor

NHS (1 mg, 9.7 μmol) and EDAC (3 mg, 16 μmol) were added to a solution of compound (3) (2.4 mg, 4.87 μmol) in DMF (0.7 ml). After 16 hours at room temperature under argon the NHS ester formation was more that 95% completed (TLC, system:BMW). The reduced and alkylated R1273 antibody (1 mg) in 1 ml of buffer (0.1 M sodium phosphate, 0.2 M sodium chloride, pH 8) was incubated with ouabain (10 mg) at room temperature for 1 hour. The inhibitor solution (20 equivalents to 900 eq/eq of antibody) was then added to the antibody and the reaction mixture was left at room temperature. After 2 hours, the mixture was either treated with NH$_2$OH.HCl (3 mg) overnight at 2° C. before dialysis or dialyzed directly against buffer (3×2.5 l, 0.1 M sodium phosphate, 0.2 M sodium chloride, pH 7.5). The conjugate solution was centrifuged and kept at 2° C. until used.

This procedure was also used to label the following: reduced and alkylated monoclonal anti-cyclosporine antibody, reduced and alkylated monoclonal anti-digoxin antibody, affinity-purified polyclonal anti-digoxin antibody, and native affinity-purified polyclonal anti-digoxin antibody.

Reduced and alkylated affinity-purified polyclonal anti-digoxin antibodies were labeled with thiogalactoside inhibitor (11) in a similar manner.

Example 7

Synthesis Of Bis-β-Alanine Digoxin Nhs Ester

Digoxin (2 g) was dissolved in a mixture of DMF (20 ml), methanol (14 ml) and water (14 ml) and treated dropwise with a solution of sodium periodate (1.434 g) in a mixture of water (10 ml) and methanol (10 ml). The solution was stirred for 3 hours at room temperature, then for 2 days at 4° C. The reaction mixture was diluted with water and extracted with ethyl acetate. The combined extracts were washed with brine, dried, and evaporated to yield the digoxin dialdehyde as an oily white solid (2 g).

Bis-β-alanine (98 mg) and sodium cyanoborohydride (40 mg) were dissolved in 0.3 M AcOH and added to a solution of digoxin dialdehyde (390 mg) in methanol (6 ml). After 3 hours, the reaction mixture was evaporated to dryness and chromatographed to give bis-β-alanine digoxin (12) (295 mg).

Bis-β-alanine digoxin (89 mg) was dissolved in DMF (1 ml) and reacted with NHS (17 mg) and EDAC (24 mg) for 16 hours at room temperature to give the bis-β-alanine digoxin NHS ester (13). Compounds (12) and (13) have the following structures:

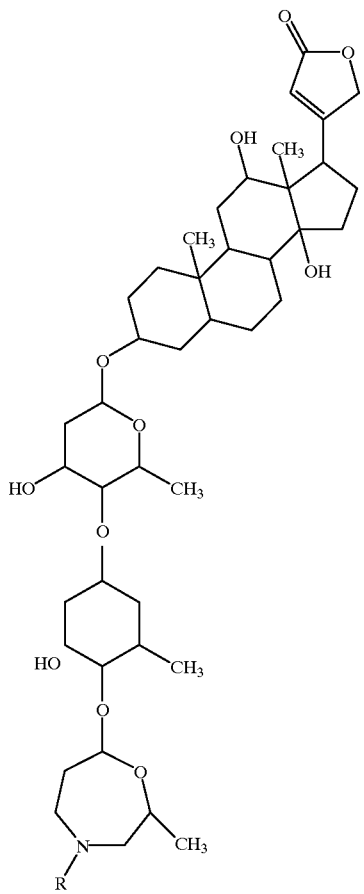

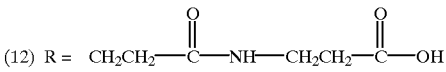
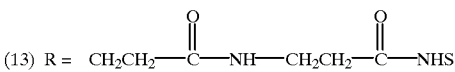
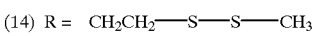
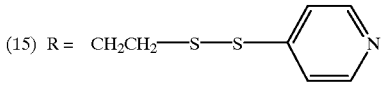
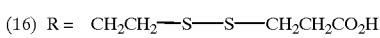
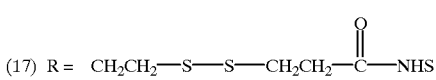

Example 8

Conjugation Of Bis-β-Alanine Digoxin To The Amine Of β-Galactosidase

*E. coli* β-galactosidase (14.7 mg) was dissolved in 2.7 ml of buffer (0.1 M sodium phosphate, 1.2 mM magnesium chloride, pH 7.6), argon degassed. 2.6 ml of this solution was treated with bromoacetic acid (0.9 ml of a 0.4 M solution in the same buffer). The solution was incubated for 4 hours at room temperature, and then excess reagents were removed by dialysis to give carboxymethylated galactosidase (3.6 mg/ml).

Carboxymethylated galactosidase (0.72 mg) dissolved in 0.2 ml of buffer (10 mM sodium phosphate, 150 mM sodium chloride, 1.0 mM magnesium chloride, pH 7.1), was treated with 22 μl of a 10 mg/ml H$_2$O solution of isopropyl-β-D-thiogalactopyranoside and the bis-β-alanine digoxin NHS ester (13) (4 μl of a 100 mM solution in DMF). The resulting solution was incubated for 4 hours. The excess reagents were removed by dialysis to give the amino-labeled digoxin-galactosidase conjugate (0.74 mg/ml).

Example 9

Synthesis Of Digoxin Disulfide Affinity Label

Digoxin dialdehyde (3.02 g) was dissolved in methanol (75 ml). 2-Methyldithioethylamine (1.0 g) and sodium cyanoborohydride (700 mg) were added, followed by a 1.0 M acetate buffer, pH 4.5 (4 ml). The resulting solution was stirred at room temperature for 40 minutes, then diluted with water and extracted with ethyl acetate. The extracts were dried, evaporated and chromatographed to give the digoxin methyl disulfide (14) (1.87 g).

The digoxin methyl disulfide (14) (412 mg) was dissolved in degassed 10% aqueous methanol (5 ml), treated with DTE (70 mg) and triethylamine (12 μl) and stored for 2 hours. The solvent was then evaporated, and the residue was dissolved in THF (6 ml) and treated with dipyridyl disulfide (106 mg). The resulting solution was stirred for 30 minutes at room temperature, then diluted with ethyl acetate and extracted with dilute aqueous sodium bicarbonate, water, and brine. The ethyl acetate solution was dried and evaporated, and the residue was chromatographed to yield the digoxin pyridyl disulfide (15) (228 mg).

The digoxin pyridyl disulfide (15) (228 mg) and 2-mercaptopropionic acid (22 μl) were dissolved in THF (6 ml) and stirred at room temperature for 30 minutes. A small additional amount of 2-mercaptopropionic acid (1 μ) was added and the solution was concentrated. The residue was chromatographed to give the digoxin disulfide acid (16).

The digoxin disulfide acid (16) (3.0 mg) was treated with a solution of EDAC (8 μmol) and NHS (17.7 μmol) in 0.2 ml DMF. After 2 hours, additional EDAC (8 μmol) and NHS (17.7 μmol) dissolved in DMF (100 μl) were added and the solution was stirred overnight. Additional EDAC (1.6 μmol) and NHS (3.5 μmol) dissolved in DMF (20 μl) were added and the mixture was stored an additional five hours, giving a solution of the digoxin disulfide NHS affinity label (17) (10.1 mM) in DMF.

Example 10

Reduction And Alkylation Of Monoclonal Anti-Digoxin Antibody

Monoclonal anti-digoxin antibody (37.6 mg) in 2.0 ml of buffer (20 mM sodium phosphate, 150 mM sodium chloride, pH 7.4) mixed with 1.6 ml of a second buffer (0.1 M sodium phosphate, 0.2 M sodium chloride, 10 mM EDTA, pH 7.4) was treated with 400 μl DTE (0.1 M in immediately preceding buffer). After incubation of the solution for five hours at room temperature, a solution of iodoacetamide (24.2 mg) in water (0.44 ml) was added and the solution was incubated for one hour at room temperature. The excess reagents were removed by dialysis to give a solution of reduced and alkylated monoclonal anti-digoxin antibody (7.8 mg/ml).

EXAMPLE 11

Affinity Labeling Of Monoclonal Anti-Digoxin Antibody With Digoxin Disulfide Affinity Label Reduced and alkylated monoclonal anti-digoxin antibody (23.4 mg) in 3.0 ml of buffer (0.01 M sodium phosphate, 0.15 M sodium chloride, pH 7.0) was treated with a solution of the digoxin disulfide NHS ester affinity label (17) (0.86 μmol) in DMF (85 μl). The resulting solution was stirred at room temperature for 3.5 hours. The excess reagents were removed by dialysis, yielding a solution of affinity-labeled monoclonal anti-digoxin antibody (6.8 mg/ml).

Example 12

Attachment Of Inhibitor To Thiol-Antibody

Affinity-labeled monoclonal anti-digoxin antibody (5.4 mg) dissolved in 0.8 ml of buffer (10 mM sodium phosphate, 150 mM sodium chloride, pH 7.3) was mixed with 50 μl of a solution of digoxin in DMF (10 mg/ml), 10 μl DMF and treated with 100 μl of a solution of DTE (25 mM) in a 0.2 M sodium chloride, 0.1 M sodium phosphate, 0.01 M EDTA, pH 7.8 buffer, and a further 40 μl of buffer. The solution was incubated for 4.5 hours at room temperature. A portion (520 μ) of the resulting solution was treated with the thiol-reactive deoxygalactostatin inhibitor (6) (80 μl of a 75 mM solution in a 50:37 methanol:water mixture) and the solution was stored overnight. The solution was then dialyzed against a 150 mM sodium chloride, 10 mM sodium phosphate, pH 7.3 buffer, filtered through a 0.20μ filter, and re-dialyzed against the same buffer to give a solution of affinity-labeled inhibitor-antibody conjugate (0.57 mg/ml).

Example 13

Removal Of Digoxin From Binding Site

The affinity-labeled inhibitor-antibody conjugate (0.57 mg in 1.0 ml) from Example 12 was mixed with a small amount of tritiated digoxin and dialyzed against 500 ml of a 10 mM MES buffer, pH 5.8, and then adsorbed onto 1 ml of ABx resin (J. T. Baker Co.) in a slurry and loaded onto a column. The column was washed with 400 ml of 10 mg/ml ouabain over the course of 4 days, at which time it was judged (by monitoring radioactivity in column effluent) that all the digoxin had been removed. The column was washed with 10 mM MES to remove excess ouabain, and then with 0.2 M sodium chloride, 0.1 M sodium phosphate, pH 7 to elute the antibody. A total of 0.28 mg of labeled antibody was recovered.

Example 14

Conjugation Of Digoxin To The Thiols Of β-Galactosidase

A solution of β-galactosidase (200 μl, 3.6 mg/ml) in argon degassed, 0.1 M sodium phosphate, 1 mM magnesium chloride, pH 8 buffer was treated sequentially with 22 μl IPTG (10 mM in above buffer) and 4.5 μl (37 mM in DMF) of the bromoacetyl digoxin derivative:

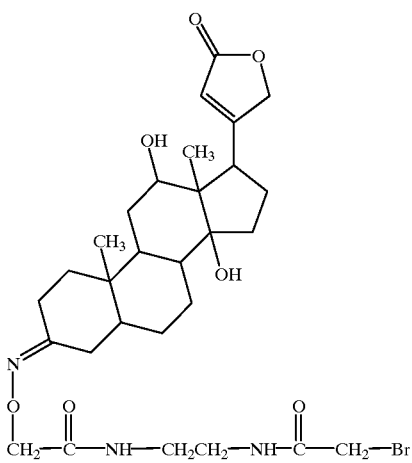

The resulting solution was incubated at room temperature for 4 hours. The solution was dialyzed against 10 mM sodium phosphate, 150 mM sodium chloride, 1 mM magnesium chloride, pH 7.4 buffer, then treated with 150 μl of a solution of 0.4 M β-mercaptoethanol in pH 9, 100 mM sodium borate buffer for 6 hours. Excess reagents were removed by dialysis against 10 mM sodium phosphate, 150 mM sodium chloride, 1 mM magnesium chloride, pH 7.4 buffer. The pH of the resulting solution was adjusted to 9.5 with 0.1 N NaOH and 10 μl of β-mercaptoethanol was added. The mixture was incubated at room temperature overnight and dialyzed to remove excess reagents to give the digoxin-galactosidase conjugate.

Example 15

Preparation Of Bromoacetylcylosporine

The compound cyclosporine (18) has the following structure:

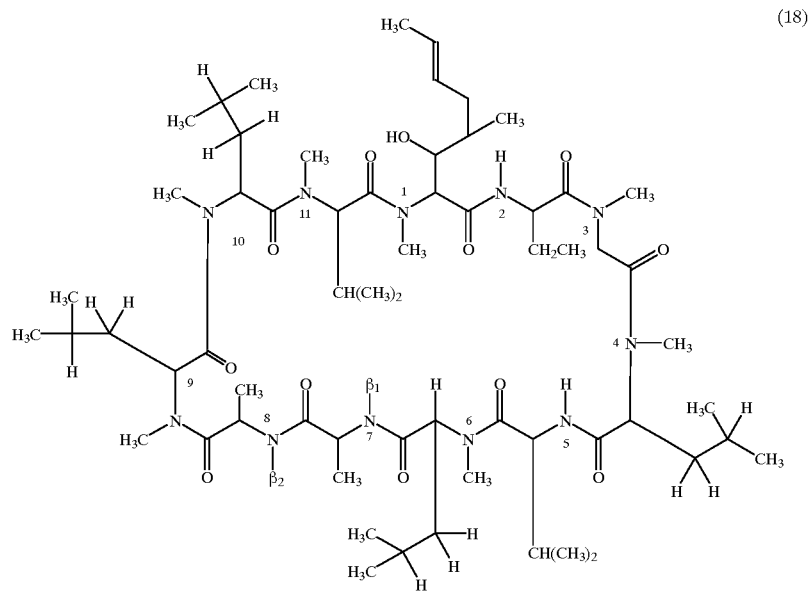

where $\beta_1$ and $\beta_2$ are hydrogen or a linking group attached to amino acid residues no. 7 and 8, respectively. For purposes of the following examples, the cyclosporine structure shall be abbreviated as:

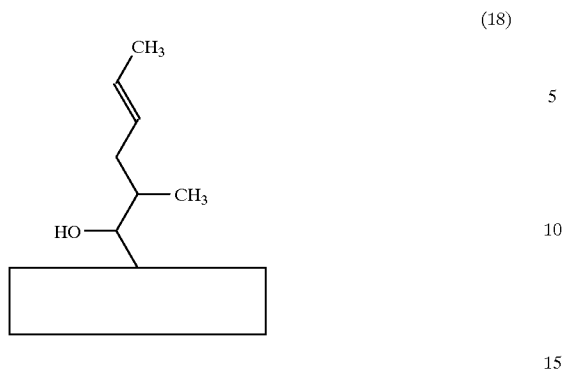
where the side chain shown is the side chain of amino acid residue no. 1.
The preparation of bromoacetylcylosporine (23) is outlined as follows:
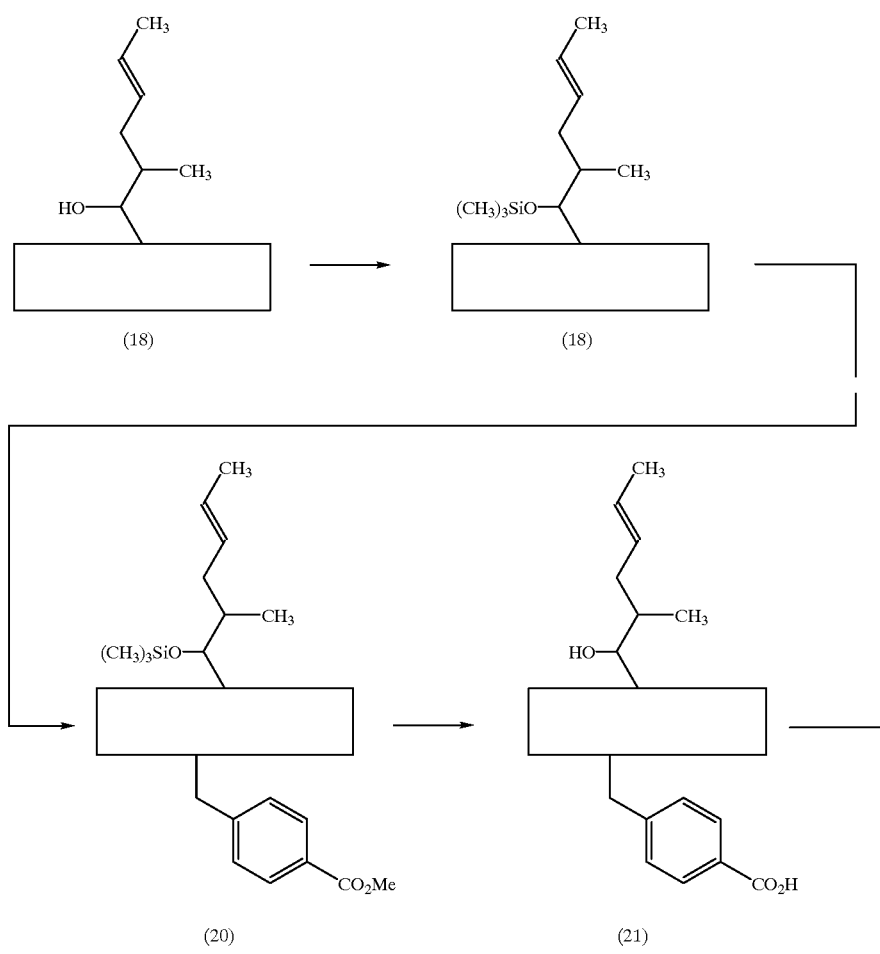

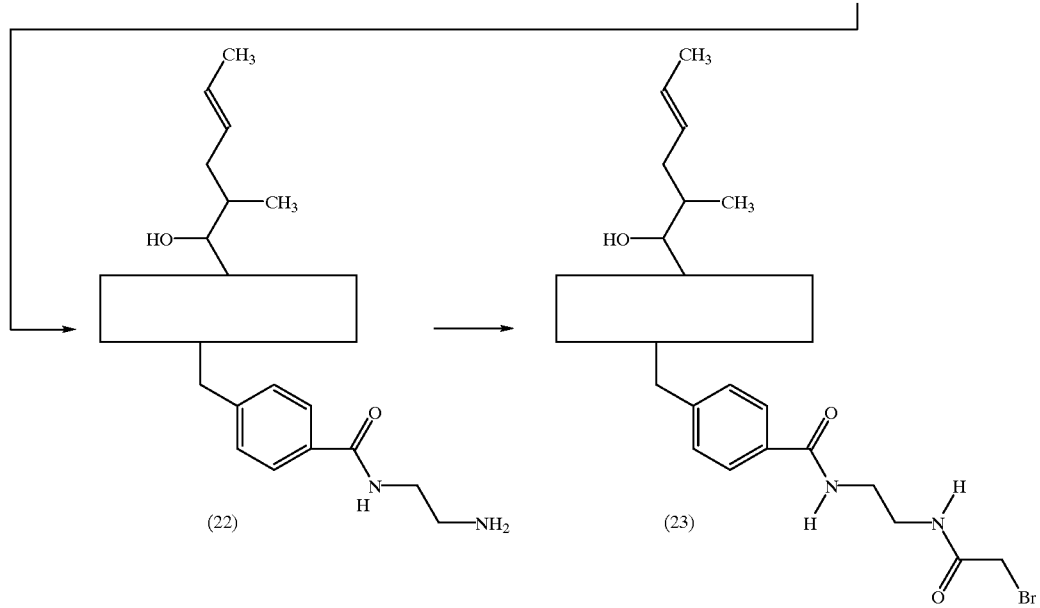

where compounds (20) through (23) are mixtures (about 50:50) of the isomer having the linking groups positioned at amino acid residue no. 7 and the isomer having the linking group positioned at amino acid residue no. 8.

THF, benzene, and toluene were dried over sodium metal and were freshly distilled prior to their use. Melting points were determined on a Thomas Hoover Capillary melting point apparatus. All the reactions were conducted under an atmosphere of dried argon.

Chlorotrimethylsilyl was added dropwise to a stirred solution of cyclosporine (18) (1800 mg) in dried pyridine (6 ml) and dried dicloromethane (6 ml) at room temperature and under an argon atmosphere. After the addition was completed, the mixture was stirred overnight. The mixture was then carefully evaporated to dryness under high vacuum and the white solid residue was then redissolved in dichloromethane and purified on a silica gel column (ethyl acetate:hexane, 80:20) to give the pure compound trimethylsilyl cyclosporine (19) (1700 mg, 89%) as a white solid. Melting point 152–156° C.

To a stirred solution of TMS-cyclosporine (19) (900 mg) in dried toluene (20 ml) was added 15-Crown-5 (Aldrich) (0.3 ml). Then, sodium hydride (350 mg, 50% suspension in mineral oil) was added at ice bath temperature under an argon atmosphere. The mixture was stirred and allowed to warm up to room temperature over a period of thirty minutes. Methyl p-(bromomethyl)-benzoate (400 mg, 2.5× 0.71 mmol) was then added, and the mixture was stirred for 24 hours at room temperature. Ethyl acetate (150 ml) was then added, followed by slow and careful addition of water (50 ml) and then hydrochloric acid (1 N) was added until the mixture was acidic (pH≅3.0). The organic layer was separated and washed with water (2×50 ml), brine (100 ml), and dried (MgSO$_4$). The solvent was then removed under reduced pressure to give the crude compound (20) as pale foam (1.3 g). The foam was then purified on PTLC (silica gel, ethyl acetate:hexane, 65:35, R$_f$≅0.6) and gave the compound methyl-p-methyl benzoate cyclosporine (20) as a white solid (670 mg, 67%).

To a stirred solution of methyl-p-methyl benzoate cyclosporine (20) (280 mg) in methanol (5 ml) was added water dropwise (≅1.5 ml) or until the solution became slightly cloudy. Potassium carbonate (anhydrous, 230 mg) was added, and the mixture was stirred for 12 hours and then water was dropwise added until the solution became slightly cloudy. Then, the mixture was stirred for another 12 hours at room temperature. To the mixture was then carefully added hydrochloric acid (1 N) until the solution became acidic (pH≅2.0). Water (50 ml) was then added and the mixture was extracted with dichloromethane (3×50 ml). The organic extracts were combined and then washed with brine (2×50 ml) and dried (MgSO$_4$). The solvent was then removed under reduced pressure to give the crude cyclosporine acid (21) (270 mg). The crude redissolved in dichloromethane (10 ml) and applied on a chromatography column (silica gel). The column first was eluted with ethyl acetate until all the starting material was eluted from the column. The column was then eluted with ethyl acetate:acetic acid (99.9:0.1) to get the cyclosporine acid (21) (160 mg, 63%) as a white solid. Melting point 171–177° C.

Hydroxysuccinamide (31.2 mg) was added to a stirred solution of the cyclosporine acid (21) (160 mg) in dried DMF (3 ml) at room temperature and an argon atmosphere. The mixture was stirred overnight. TLC (silica gel, MeOH:CH$_2$Cl$_2$:AcOH, 10:90:0.1) indicated complete conversion of the acid to the NHS ester.

To a solution of ethylene diamine (180 mg) in dried THF (3 ml) was added the above NHS ester solution over a period of 30 minutes. The reaction mixture was stirred for 1 hour and then was diluted with ethyl acetate (50 ml). The organic phase was washed with water (3×50 ml) and dried (MgSO$_4$). The solvent was then evaporated to dryness to give the cyclosporine amine product (22) as a white powder (170 mg, 99%).

To a stirred solution of the radio-labeled bromoacetic acid (C-1*, specific activity 55 mCi/mol, 0.625 mg) in CH$_2$Cl$_2$ (3 ml) was added cold bromoacetic acid (17.9 mg, total amount of bromoacetic acid 18.5 mg). To the resulting mixture was added NHS (16.5 mg) and DCC (29.5 mg) at ice bath temperature and under an argon atmosphere. The mixture was stirred overnight and then a solution of the cyclosporine amine (22) (90 mg) in CH$_2$Cl$_2$ (2 ml) was added. The mixture was stirred for 3 hours. Ethyl acetate (25 ml) was added and the organic phase was washed with water (3×50 ml) and dried (MgSO$_4$). The solvent was then removed under the reduced pressure and the residue was purified on PTLC (silica gel, ethyl acetate:MeOH, 90:10) to give the product (23) (87 mg, 89%, specific activity 11.58×10$^8$ CPM/mmol).

Example 16

Conjugation Of The Bromoacetyl Cyclosporine To β-Galactosidase

A solution of β-galactosidase (5 mg, 9.0 nmol) was dissolved in degased phosphate buffer (5 ml, 100 mM phosphate, 1.0 mM MgCl$_2$, 0.1% Pluronic, pH 8.0). The enzyme solution was divided into five 1.0 ml solutions. Methanol (200, 167, 133, 66, 0 μl) was added to the enzyme solution respectively. To these enzyme solutions was added a solution of the bromoacetyl cyclosporine (23) (2 mg/ml) in methanol (0, 33, 67, 134, 269 μl) respectively. At the end of this addition each enzyme solution contained approximately 20% of methanol and 0, 25, 50, 100 and 200, equivalents of the bromoacetyl cyclosporine, respectively. The enzyme solutions were then incubated at 37° C. overnight. The samples were then dialyzed against phosphate buffer (100 mM, pH 7.3, 0.1% Pluronic 25R2, mercaptoethanol 1 mM, MgCl$_2$ 1 MM). The resulting enzyme conjugates were shown to have 0, 6, 10, 11 and 24, cyclosporine per enzyme, respectively.

Example 17

Preparation Of The Cyclosporine Carbamate

The preparation of cyclosporine carbamate (26) is outlined as follows:

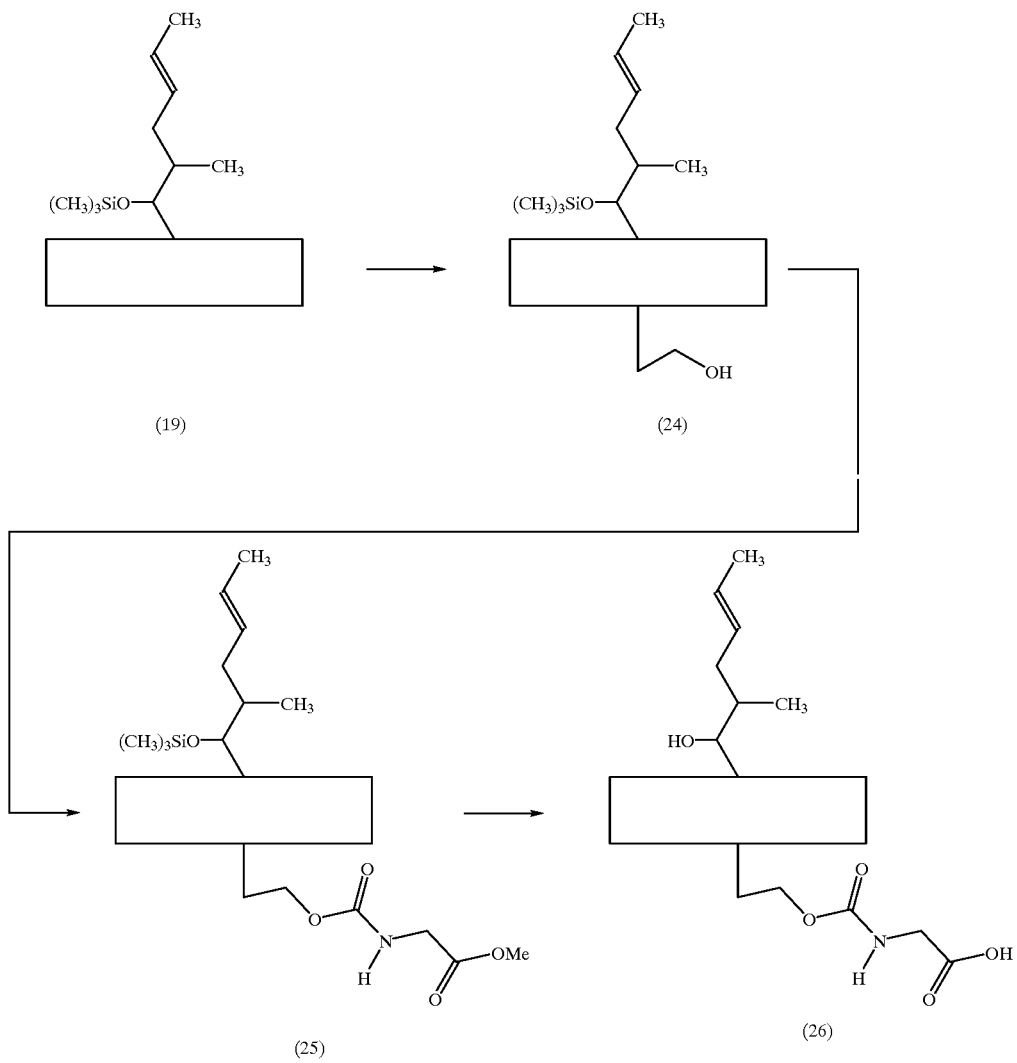

where the linking groups of compounds (24) through (26) are positioned at amino acid residue no. 7.

Sodium hydride (450 mg, 50% suspension in mineral oil) was added to a stirred solution of TMS-cyclosporine (19) (1000 mg) and 15-Crown-5 (Aldrich) (0.2 ml) in dried toluene (30 ml) at room temperature under an argon atmosphere. After 30 minutes, the reaction mixture was cold at 4° C. and ethylene oxide (Fluka) (6 ml) was added via a syringe. The reaction flask was then capped (sealed by stopper and parafilm) and stirred at room temperature for 24 hours. The reaction mixture was then treated very carefully with water (100 ml) and was then acidified with hydrochloric acid (1 N) and dichloromethane (200 ml) was then added. The organic layer was separated and washed with water (100 ml) and dried (MgSO$_4$). The solvent was then removed under reduced pressure to give the crude product as a white solid. The crude product was purified using column chromatography (silica gel, ethyl acetate) to give hydroxyethyl cyclosporine (24) as a white solid (350 mg, 34%). Melting point 124–132° C.

Methyl glycinate isocyanate was added to a stirred solution of hydroxyethyl cyclosporine (24) (300 mg, 0.23 mmol) and tri n-butyl tin ethoxide (Aldrich) (154 mg, 0.4 mmol) in dried toluene (2 ml) at room temperature and under an argon atmosphere. The reaction mixture was stirred for 2 hours. Ethyl acetate (50 ml) and water (50 ml) was then added. The organic layer was separated and washed with a brine:water mixture (1:1, 2×50 ml) and dried (MgSO$_4$). The organic phase was removed under reduced pressure, and the foamy solid was purified by column chromatography (silica gel, ethyl acetate) to give the pure cyclosporine ester derivative (25) (280 mg, 85%).

Water was added to a stirred solution of the ester (25) (250 mg) in methanol (10 ml) until the mixture became slightly cloudy. Potassium carbonate (200 mg, anhydrous) was then added, and the mixture was stirred overnight at room temperature under an argon atmosphere. The mixture was then acidified with hydrochloric acid (1 N) and water (20 ml) was added. The mixture was then extracted with dichloromethane (3×75 ml). The combined organic extract was washed with brine (100 ml) and dried (MgSO$_4$). The solvent was then removed under reduced pressure to give hydroxyethyl carbamate acid (26) as a white solid (220 mg, 96%). Melting point 156–166° C.

Example 18

Conjugation Of Cyclosporine Carbamate To β-Galactosidase

Cyclosporine carbamate acid (26) was reacted with DCC and NHS in DMF to yield a solution of the NHS ester (13.5 mg/ml) in DMF.

A solution of β-galactosidase (5 mg) was dissolved in degassed phosphate buffer (5 ml, 100 mM phosphate, 1.0 mM MgCl$_2$, 0.1% Pluronic 25R2, pH 8.0). The enzyme solution was divided into five 1.0 ml solutions. Methanol (200, 197, 195, 190, and 180 µl) was added to the enzyme solution respectively. To these enzyme solutions was added a solution of the cyclosporine carbamate-NHS ester (13.5 mg/ml, 0.01 mM) in dried DMF (0, 2.5, 5, 10 and 20 µl, respectively). At the end of these additions each enzyme solution contained approximately 20% of methanol and 0, 25, 50, 100 and 200 equivalents of the cyclosporine carbamate, respectively. The enzyme solutions were then incubated at 4° C. overnight. The enzyme solutions were then dialyzed against phosphate buffer (100 mM, pH 7.3, 0.1% Pluronic 25R2, MgCl$_2$ 1 mM) three times. The concentration of each sample was determined (by U.V.) to be 0.7 mg/ml.

Example 19

Assay For Digoxin Using Randomly Labeled Anti-Digoxin Antibody-Deoxygalactostatin Inhibitor Conjugate And Thiol-Labeled Digoxin-Galactosidase Conjugate The assay buffer was 0.1 M sodium phosphate, 1 mM magnesium chloride, pH 7.5, and contained 1 mg/ml bovine serum albumin. Affinity purified unreduced polyclonal antibody (R1273) was used. The randomly-labeled inhibitor-antibody conjugate (50 µl of a 400 nM solution) and sample (50 µl) were mixed with assay buffer (400 µl) and incubated for 10 minutes at room temperature. Thiol-labeled digoxin-galactosidase conjugate (50 µl of a 0.25 nM solution) and additional assay buffer (200 µl) were added, and the resulting solution was incubated for 20 minutes at room temperature. Enzymatic activity at 37° C. was determined by adding chlorophenol red galactoside (50 µl of a 0.13 M solution) and additional assay buffer (200 µl) and measuring the rate of absorbance increase at 575 nm in a thermostatted spectrophotometer. The enzymatic activity was a function of digoxin concentration, as shown below.

| Concentration of digoxin in sample (µM) | Enzymatic Activity (mA/min) |
| --- | --- |
| 0 | 58 |
| 2 | 89 |
| No antibody added | 97 |

Example 20

Assay For Digoxin Using Affinity-Labeled Deoxygalactostatin Inhibitor-Antibody Conjugate And Amine-Labeled Digoxin-Galactosidase Conjugate The assay buffer was 0.1 M sodium phosphate, 1 mM magnesium chloride, pH 7.5, and contained 1 mg/ml bovine serum albumin. Affinity-labeled inhibitor-antibody conjugate (50 µl of a 1.06 µM solution) and sample (50 µl) were mixed with assay buffer (400 µl) and incubated for 2 minutes at room temperature. Digoxin-labeled galactosidase (50 µl of a 1 nM solution) and additional assay buffer (200 µl) were added, and the resulting solution was incubated for 1 hour at room temperature. Enzymatic activity at 25° C. was determined by adding ONPG (50 µl of a 0.6 mM solution) and additional assay buffer (200 µl) and measuring the rate of absorbance increase at 405 nm in a thermostatted spectrophotometer. The enzymatic activity was a function of digoxin concentration, as shown below:

| Concentration of digoxin in sample (µM) | Enzymatic Activity (mA/min) |
| --- | --- |
| 0 | 48 |
| 0.475 | 57 |
| No antibody added | 72 |

Example 21

Assay For Cyclosporine Using Randomly-Labeled Anti-Cyclosporine Antibody-Deoxygalactostatin Inhibitor Conjugate And Amine-Labeled Cyclosporine-Galactosidase Conjugate The assay buffer was 0.1 M sodium phosphate, 1 mM magnesium chloride, pH 7.1, and contained 1 mg/ml bovine serum albumin. The antibody used was monoclonal reduced and alkylated anti-cyclosporin antibody. The randomly-labeled anti-cyclosporine antibody-inhibitor conjugate (50 µl of a 12.5 nM solution) and sample (50 µl of a solution of cyclosporine dissolved in a 55 mM tris, pH 8.0 buffer, containing 0.05% Pluronic 25R2) were mixed with assay buffer (400 μl) and incubated for 2 minutes at room temperature. Amine-labeled cyclosporine-galactosidase conjugate (50 μl of a 5 nM solution) and additional assay buffer (200 μl) were added, and the resulting solution was incubated for 15 minutes at room temperature. Enzymatic activity at 37° C. was determined by adding chlorophenol red galactoside (50 μl of a 40 mg/ml solution) and additional assay buffer (200 μl) and measuring the rate of absorbance increase at 575 nm in a thermostatted spectrophotometer. The enzymatic activity was a function of cyclosporine concentration, as shown below:

| Concentration of cyclosporin in sample (nM) | Enzymatic Activity (mA/min) |
|---|---|
| 0 | 198 |
| 4 | 200 |
| 8.3 | 205 |
| 17 | 211 |
| 33 | 214 |
| 58 | 219 |
| 83 | 220 |
| No antibody added | 222 |

Example 22

Assay For Cyclosporine Using Randomly-Labeled Anti-Cyclosporine Antibody-Deoxygalactostatin Inhibitor Conjugate And Thiol-Labeled Cyclosporine-Galactosidase Conjugate The assay buffer was 0.1 M sodium phosphate, 1 mM magnesium chloride, pH 7.1, and contained 1 mg/ml bovine serum albumin. The antibody used was monoclonal reduced and alkylated anti-cyclosporin antibody. The randomly-labeled anti-cyclosporine antibody-inhibitor conjugate (50 μl of an 100 nM solution) and sample (50 μl of a solution of cyclosporine dissolved in a 55 mM tris, pH 8.0 buffer, containing 0.05% Pluronic 25R2) were mixed with assay buffer (400 μl) and incubated for 2 minutes at room temperature. Thiol-labeled cyclosporine-galactosidase conjugate (50 μl of an 8 nM solution) and additional assay buffer (200 μl) were added, and the resulting solution was incubated for 15 minutes at room temperature. Enzymatic activity at 37° C. was determined by adding chlorophenol red galactoside (50 μl of a 40 mg/ml solution) and additional assay buffer (200 μl) and measuring the rate of absorbance increase at 575 nm in a thermostatted spectrophotometer. The enzymatic activity was a function of cyclosporine concentration, as shown below:

| Concentration of cyclosporin in sample (nM) | Enzymatic Activity (mA/min) |
|---|---|
| 0 | 166 |
| 333 | 203 |
| No antibody added | 214 |

Example 23

Assays For Digoxin Using Randomly Labeled Reduced And Alkylated Polyclonal Anti-Digoxin Antibody-Inhibitor Conjugates And Amine-Labeled Digoxin Galactosidase Conjugate The assay buffer was 0.08 M sodium phosphate, 0.12 M potassium phosphate, 0.02 M sodium azide, 8 mM EGTA, 1.7 mM magnesium acetate, 1% ethylene glycol, 0.04% Tween 20, 0.005% polyoxyethylene 9 lauryl ether, 0.01% Pluronic 25R2, pH 7.0.

Sample (digoxin calibrators, Syva Company, 25 μl), randomly-labeled anti-digoxin galactostatin-antibody conjugate (100 μl of a 0.5 nM solution) and water (25 μl) were mixed and incubated for either 125 or 195 seconds at 37° C. Amine-labeled digoxin-galactosidase conjugate (25 μl) were added, and the resulting solution was incubated for 100 seconds at 37° C. Enzymatic activity at 37° C. was determined by adding chlorophenol red galactoside (12.5 μl of a 98 mM solution) and additional water (37.5 μl) and measuring the rate of absorbance increase at 550 nm in a thermostatted spectrophotometer. The enzymatic activity was a function of digoxin concentration.

The following data is from an assay using deoxygalactostatin inhibitor-labeled native polyclonal antibody. The sample and antibody were incubated for 125 seconds.

| Concentration of digoxin in sample (ng/ml) | Enzymatic Activity (mA/min) |
|---|---|
| 0 | 68 |
| 0.5 | 70 |
| 1 | 71 |
| 2 | 75 |
| 3 | 75.5 |
| 4 | 77 |
| No antibody added | 82 |

The following data is from an assay for digoxin using deoxygalactostatin inhibitor-labeled reduced and alkylated polyclonal antibody. The sample and antibody were incubated for 125 seconds.

| Concentration of digoxin in sample (ng/ml) | Enzymatic Activity (mA/min) |
|---|---|
| 0 | 52 |
| 0.5 | 55 |
| 1 | 58 |
| 2 | 66 |
| 3 | 70 |
| 4 | 74 |
| No antibody added | 82 |

The following data is from an assay for digoxin using thiogalactoside inhibitor-labeled reduced and alkylated polyclonal antibody. The sample and antibody were incubated for 975 seconds.

| Concentration of digoxin in sample (ng/ml) | Enzymatic Activity (mA/min) |
|---|---|
| 0 | 51 |
| 0.5 | 53 |
| 1 | 54 |
| 2 | 60 |
| 3 | 68 |
| 4 | 68.5 |
| No antibody added | 82 |

The following data is from an assay for digoxin using deoxygalactostatin inhibitor-labeled reduced and alkylated monoclonal antibody. The sample and antibody were incubated for 975 seconds.

| Concentration of digoxin in sample (ng/ml) | Enzymatic Activity (mA/min) |
|---|---|
| 0 | 57.5 |
| 0.5 | 58.7 |
| 1 | 58.9 |
| 2 | 63.7 |
| 3 | 64.6 |
| 4 | 66.7 |
| No antibody added | 82 |

Example 24

Preparation Of Acetylcholinesterase Inhibitor-Labeled Antibody 1,10-Diaminodecane is warmed in ethanol with 1 equivalent of the ethyl ester of succinic acid monoaldehyde. Sodium cyanoborohydride (4 equivalents) is then added and the solution allowed to stand for 24 hours at room temperature, while the pH is kept at 6 by adding aqueous HCl.

The reaction mixture is diluted with aqueous sodium carbonate and the product extracted with methyl chloride. The combined organic extracts are dried ($Na_2SO_4$) and evaporated to dryness to yield the ethyl ester of N-carboxypropyl-1,10-diaminodecane.

The residue is dissolved in DMF and methyl iodide (100 equivalents) and 1,2,2,6,6-pentamethylpiperidine (10 equivalents) are added. See Sommer, et al., *J. Org. Chem.* 36:824 (1971). After a few hours, acetone is added and the precipitate filtered. The residue is then refluxed with 6% DMF in acetone for one hour, filtered and washed with acetone to provide N-carboxypropyl-N,N,N',N',N'-pentamethyl-1,10-diaminodecane ethyl ester (also known as the ethyl ester of N-carboxypropyl-N,N,N',N',N'-pentamethyl-1,10-decanediaminium iodide). The ester is dissolved in sodium hydroxide (0.1 M) and after one hour, the solution is acidified to pH 3 with HCl (1 N), filtered and lyophilized. The remaining acid is dissolved in DMSO. The activation into its NHS ester and the labeling of anti-digoxin antibody is performed as in Example 6.

Example 25

Preparation Of Digoxin-Labeled Acetylcholinesterase

This is accomplished as set forth in Example 8 for the labeling of β-galactosidase.

Example 26

Assay For Digoxin Using Inhibitor-Labeled Antibodies To Digoxin And Digoxin-Labeled Acetylcholinesterase The assay buffer is 0.1 M sodium phosphate, 0.1 M potassium chloride, pH 8, containing 1 mg/ml bovine serum albumin. Randomly-labeled inhibitor-antibody conjugate (50 µl of a 400 mM solution) and sample (50 µl) are mixed with assay buffer (400 µl) an incubated for 10 minutes at room temperature. Digoxin-labeled acetylcholinesterase conjugate (50 µl of a 1.5 units per ml solution) and additional assay buffer (200 µl) is added and the resulting solution is incubated for 20 minutes at room temperature. Enzymatic activity at 25° C. is determined by adding 50 µl of a solution of acetylthiocholine iodide (8 mM) and 5,5-dithio-bis-(2-nitrobenzoic acid) (6.4 mM) in phosphate buffer (0.1 M, pH 7) and additional assay buffer (200 µl). The rate of absorbance increase is measured at 410 nm at 25° C. The enzyme activity is a function of digoxin concentration.

Although the foregoing invention has been described in some detail by way of illustration and example for the purposes of clarity and understanding, it will be obvious that certain changes or modifications may be practiced within the scope of the appended claims.

What is claimed is:

1. A method for determining the presence of an analyte in a sample suspected of containing said analyte, which comprises:
   (a) bringing together in an aqueous medium, said sample, an enzyme bound to a first specific binding pair member, and an inhibitor for said enzyme bound to a second specific binding pair member, wherein said specific binding pair members are each capable of binding to said analyte or to an sbp member complementary to said analyte;
   (b) analyzing said medium for the activity of said enzyme by measuring the conversion of a substrate for said enzyme to a product; and
   (c) relating said activity to the amount of analyte present in said medium.

2. The method of claim 1 wherein said enzyme is bound to at least one molecule of said first specific binding pair member.

3. The method of claim 2 wherein said enzyme has at least three molecules of said first specific binding pair member bound per catalytic site of said enzyme.

4. The method of claim 1 wherein at least one molecule of said inhibitor is bound per binding site of said second specific binding pair member.

5. The method of claim 1 wherein said first specific binding pair member is analogous to said analyte and said second specific binding pair member is complementary to said analyte.

6. The method of claim 1 wherein said enzyme is covalently bound to said first specific binding pair member and said inhibitor is covalently bound to said second specific binding pair member.

7. The method of claim 1 wherein at least three molecules of said inhibitor are bound per binding site of said second specific binding pair member.

8. The method of claim 1 wherein said second specific binding pair member is an antibody and said first specific binding pair member is an antigen.

9. The method of claim 1 wherein said inhibitor bound to said second specific binding pair member binds to said enzyme with a dissociation constant in the range of $10^{-2}$ to $10^{-8}$ M when said first specific binding pair member is not otherwise bound to said enzyme.

10. The method of claim 1 wherein said inhibitor has a molecular weight less than 2000.

11. The method of claim 1 wherein said enzyme is β-galactosidase.

12. The method of claim 11 wherein said enzyme inhibitor is selected from the group consisting of substituted piperidines and substituted pyrans.

13. The method of claim 1 wherein said analyte is a drug or drug metabolite.

14. The method of claim 13 wherein said drug is digoxin.

15. The method of claim 13 wherein said drug is cyclosporin.

16. An immunoassay for determining the presence of an analyte in a sample suspected of containing said analyte, which comprises:

bringing together in an aqueous medium, said sample, a first conjugate of an enzyme with an analyte analog and a second conjugate of an inhibitor for said enzyme with an antibody to said analyte wherein binding of said antibody to said analyte analog is modulated by the presence of analyte in said medium; and determining the enzymatic activity of said medium by measuring the conversion of a substrate for said enzyme to a product.

17. A composition of matter comprising a solution containing an antigen bound to an enzyme and an antibody for said antigen bound to a reversible inhibitor for said enzyme.

18. The composition of claim 17 wherein said antigen is covalently bound to said enzyme and said antibody is covalently bound to said inhibitor.

19. A composition comprising a solution containing a drug having a molecular weight of about 100 to 2000 covalently bound to an enzyme and an antibody to said drug covalently bound to an inhibitor for said enzyme.

20. The composition of claim 19 wherein said inhibitor is a competitive inhibitor.

21. A composition comprised of a solution containing a drug having a molecular weight of about 100 to 2000 bound to β-galactosidase, and an antibody to said drug bound to an inhibitor for said β-galactosidase.

22. The composition of claim 21 wherein said inhibitor is a competitive inhibitor.

23. The composition of claim 21 wherein said drug is digoxin.

24. The composition of claim 21 wherein said drug is cyclosporin.

25. A kit for carrying out an immunoassay for an analyte comprising in packaged form a first conjugate of a first specific binding pair member with an enzyme and a second conjugate of a second specific binding pair member with an inhibitor for said enzyme.

26. The kit of claim 25 wherein said first specific binding pair member is an antigen.

27. The kit of claim 26 wherein said second specific binding pair member is an antibody to said antigen.

* * * * *